(12) United States Patent
Chen et al.

(10) Patent No.: US 11,291,854 B2
(45) Date of Patent: Apr. 5, 2022

(54) EIGHT-TRIGRAMS BASED FIVE-COLOR PHOTOTHERAPY DEVICE FOR BODY HEALING AND BALANCE

(71) Applicants: Alex Chia-Hwang Chen, Johns Creek, GA (US); Zhaozhang Wang, Tainan (TW)

(72) Inventors: Alex Chia-Hwang Chen, Johns Creek, GA (US); Zhaozhang Wang, Tainan (TW)

(73) Assignee: PhotonFECT Technology, LLC., Johns Creek, GA (US)

( * ) Notice: Subject to any disclaimer, the term of this patent is extended or adjusted under 35 U.S.C. 154(b) by 0 days.

(21) Appl. No.: 17/082,084

(22) Filed: Oct. 28, 2020

(65) Prior Publication Data
US 2021/0128934 A1    May 6, 2021

Related U.S. Application Data

(60) Provisional application No. 62/931,285, filed on Nov. 6, 2019.

(51) Int. Cl.
*A61N 5/06* (2006.01)

(52) U.S. Cl.
CPC ...... *A61N 5/062* (2013.01); *A61N 2005/0626* (2013.01); *A61N 2005/0644* (2013.01); *A61N 2005/0647* (2013.01); *A61N 2005/0651* (2013.01); *A61N 2005/0663* (2013.01)

(58) Field of Classification Search
CPC ............ A61N 5/062; A61N 2005/0663; A61N 2005/0647; A61N 2005/0651; A61N 2005/0644; A61N 2005/0626; A61N 5/0619
See application file for complete search history.

(56) References Cited

U.S. PATENT DOCUMENTS

| | | | |
|---|---|---|---|
| 2007/0208395 A1* | 9/2007 | Leclerc | A61N 5/0616 607/86 |
| 2017/0118838 A1* | 4/2017 | Williams | H05K 3/32 |

OTHER PUBLICATIONS

P.K. Odle; "8 Trigrams of the Yi Jing"; http://www.fengshuiadvantage.com/articles/8trigramsoftheyijing.html (Year: 2007).*
D.H. Van den Berghe; "The true colors of the trigrams" www.fourpillars.net (Year: 1998).*

* cited by examiner

*Primary Examiner* — Brian T Gedeon
*Assistant Examiner* — Joshua Andrew Schum-Houck
(74) *Attorney, Agent, or Firm* — Limin Wen

(57) ABSTRACT

Based on traditional Chinese medicine and ancient Eight-Trigram theory, a wearable five-color phototherapy device is invented for a unique painless, drug-free, non-invasive, and true green organic therapy by using light energy on some particular areas of a person's skin. There are multiple light-emitting components which is a number of light-emitting elements arranged in each of Eight-Trigram positions are designed on the bottom of this device. These multiple light-emitting components produce color of red or green or white or yellow or black or no color in each of Eight-Trigram positions. A software or App is developed to directly or remotely control and communicate with such device and provide the optimal solution for the five-color phototherapy.

1 Claim, 6 Drawing Sheets

Fig. 1

| 4 | 5 | 6 |
|---|---|---|
| 3 |   | 7 |
| 2 | 1 | 8 |

Fig. 2

| LV | HT | SP |
|---|---|---|
| GB |   | LU |
| ST | KD/BL | LI |

Fig. 3

| Wood | Fire | Earth |
|---|---|---|
| Wood |   | Metal |
| Earth | Water | Metal |

Fig. 4

| Green | Red | Yellow |
|---|---|---|
| Green |   | White |
| Yellow | Black | White |

Fig. 5

| White<br>Black<br>Red<br>Yellow<br>Green<br>Empty | White<br>Black<br>Red<br>Yellow<br>Green<br>Empty | White<br>Black<br>Red<br>Yellow<br>Green<br>Empty |
|---|---|---|
| White<br>Black<br>Red<br>Yellow<br>Green<br>Empty | | White<br>Black<br>Red<br>Yellow<br>Green<br>Empty |
| White<br>Black<br>Red<br>Yellow<br>Green<br>Empty | White<br>Black<br>Red<br>Yellow<br>Green<br>Empty | White<br>Black<br>Red<br>Yellow<br>Green<br>Empty |

Fig. 6

EIGHT-TRIGRAMS BASED FIVE-COLOR PHOTOTHERAPY DEVICE FOR BODY HEALING AND BALANCE

REFERENCE TO RELATED APPLICATION

This application claims the benefit of the filing date of US Provisional Patent Application Ser. No. 62/931,285 filed on Nov. 6, 2019, entitled "Eight-Trigrams Based Five-Color Phototherapy Device For Body Healing and Balance". The teachings of the entire referenced application are incorporated herein by reference.

FIELD OF THE INVENTION

This invention relates generally to medical therapy devices, more specifically a five-color lighting therapy device with one or multiple light-emitting components positioned in Eight-Trigrams positions is disclosed, wherein the light-emitting component(s) are configured to have direct contact with the skin of the user without any intermediary materials and light the surface for photodynamic stimulation of the body, wherein the therapy device contains an arrangement of multiple light-emitting components on a circuit board in an Eight-Trigram positions to provide five-color lighting energy healing capability over the skin.

BACKGROUND OF THE INVENTION

Five Element Color Therapy is a healing method derived from the traditional Chinese medicine. At its core, it is based on the theory of Yin-Yang, Five Elements and Eight Trigrams (Ba Gua) of Chinese medicine. It utilizes the spectral energy of color to certain area of the human body to adjust the flow of Qi, in order to bring about an optimal state of physical and mental balance and open up the healing process. Five Element Color Therapy was created by Master Zhaozhang Wang. He devoted decades of his time and energy to research and practice the ancient traditional Chinese medicine, eventually created the unique painless, drug-free, non-invasive, and true green organic therapy. After nearly twenty years of application in many areas around the world with more than ten thousand clinical cases covering from minor pain to critical diseases, it has shown that the Five Element Color Therapy is practical, convenient and effective.

Light energy is a form of electro-magnetic radiation. Light travels in waves and is the only form of energy visible to the human eyes. All creatures and plants on the earth rely on the energy from the sunlight to produce their own energy (See Color wavelength below).

| Color | Wavelength |
| --- | --- |
| Red | ~700-635 nm |
| Yellow | ~590-560 nm |
| Green | ~560-520 nm |
| White | ~390-700 nm |
| Black | ~100-400 nm |

Different kind of energy contributes to become a huge consolidated energy field in the environment. This is known as ecology.

During the absence of the sunshine, the energy field changes accordingly. So, the energy level changes as the amount of the sunlight varies.

In the traditional Chinese medicine philosophy, five colors (green, red, yellow, white and black) represent five directions. The East is green, the South is red, the West is White, the North is black, and the Center is yellow. The ancient Chinese medicine theory regarded these five colors as the primary colors and they correspond to the Five Elements respectively: Wood (green), Fire (red), Earth (yellow), Metal (white), and Water (black). As color comes from light refraction and light is a kind of energy, colors carry the energy and have an impact to the human body.

The Eight Trigrams represents eight natural phenomena: heaven, earth, thunder, wind, mountain, swamp, water and fire. They correspond to the Five Elements of the ancient Chinese medicine theory.

The human body is an Eight Trigrams system and many parts of the body carry the holographic of Eight Trigrams. Eight Trigrams embodies the relevance and wholeness of the human body. The Eight Trigrams of the Human body reflects Ancient Chinese sophists of "nature and human unite as one".

Color Therapy

In the five-element color therapy, colors are applied on the abdomen or palm of the human body, under the guidance of the Eight Trigrams theory and diagnosis in the traditional Chinese medicine.

Since each symbol of the Eight Trigrams represents one or two organs of the human body, respective colors work on our body as medicines do by generating, restricting, strengthening and neutralizing the organs' energy, trying to bring the body into a more balanced and healthy state and open up the healing process to cure the disease (See FIG. 1-8).

The above Five Element Color Therapy fully rely on the nature lights and be passive way to bring the body back to balance.

The Five Elements refer to five categories in the natural world, namely wood, fire, earth, metal and water. The theory of the five elements holds that all phenomena in the universe correspond in nature either to wood, fire, earth, metal or water, and that these are in a state of constant motion and changes.

Law of movement of the Five Elements mainly manifests in the following ways: promoting, overacting, counteracting and insulting over mutual relation like between mother and son.

Promoting implies promoting growth. Wood promotes fire, fire promotes earth, earth promotes metal, metal promotes water, and water, in turn, promotes wood. This promoting relationship of the five elements is known as the "mother-son" relationship. Overacting means bringing under control or restraint. In the overacting relationship, wood acts on earth, earth acts on water, water acts on fire, fire acts on metal, and metal in turn acts on wood. Insulting means counter promoting or restraint. In the Insulting relationship, wood insults on water, water insult on metal, metal insults on earth, earth insults on fire, and fire in turn insults on wood. Counteracting means the reverse control under Overacting to reduce the overacting or restraint. In the counteracting relationship, wood counteracts on metal, metal overacts on fire, fire overacts on water, water overacts on earth, and earth in turn overacts on wood.

By putting different color on each Trigrams position will create the Five Elements relationship in promoting, overacting, counteracting or insulting effect to bring the internal organs back to normal stage and to heal the body.

In order to implement Five Element Color Therapy Healing Method, the tools like Face Deco Crayons or Colorful Kinesiology Tapes are used as the media applied to Human Body either on the Palm or Abdomen Area.

Those tools are simply with five (5) different colors as "RED", "YELLOW", "GREEN", "WHITE", and "BLACK" so that Five Element Color Therapy can be performed.

As the Crayons or Tapes are fully relied on the nature lights to provide the Energy Source for the treatment, moreover, during the healing course, Crayons color can be easily wiped out and the Tapes can easily cause rashes on the skin, a new method will be in need to enhance the performance, effectiveness and long duration of usage in healing.

BRIEF DESCRIPTION OF THE DRAWINGS

FIG. 1 is a top perspective view of the empty Eight-Trigrams illustration.

FIG. 2 is a top perspective view of the Eight-Trigrams Position illustration.

FIG. 3 is a top perspective view of the Eight-Trigram Position and Assigned Internal Organs Relationship Illustration, where each Abbreviation represents:

| | | | | |
|---|---|---|---|---|
| LV: Liver | HT: Heart | SP: Spleen | GB: Gall Bladder | LU: Lung |
| ST: Stomach | LI: Large Intestine | KD: Kidney | | BL: Bladder |

FIG. 4 is a top perspective view of the Eight-Trigram Positions and Assigned Five-Elements Relationship illustration.

FIG. 5 is a top perspective view of the Eight-Trigram Positions and Assigned Five Color Relationship illustration.

FIG. 6 is a top perspective view of the Eight-Trigrams with 5-Color Combination illustration.

Figure 7:
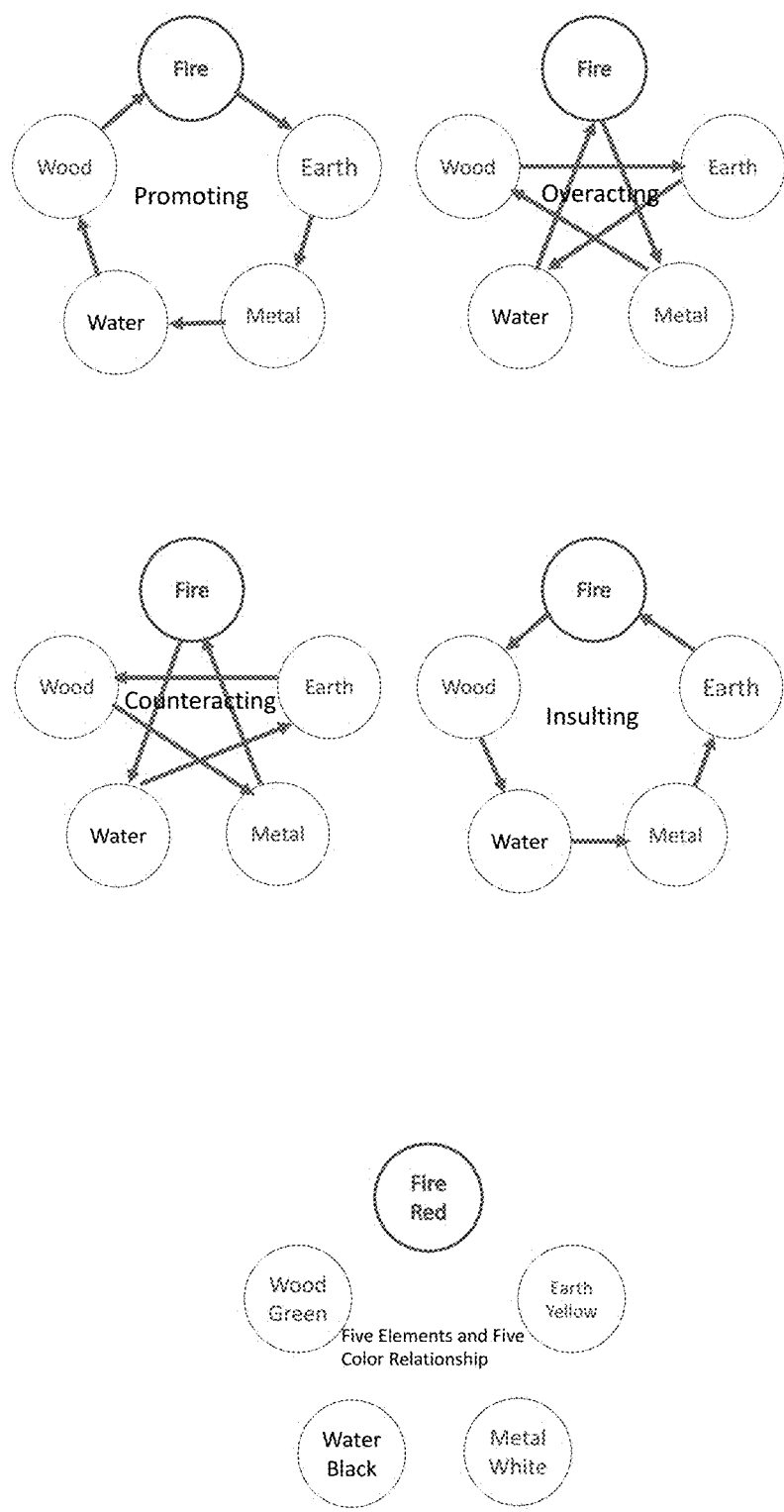

FIG. 7 is diagrams of the relationships of the Five Elements and Five Colors.

Figure 8:
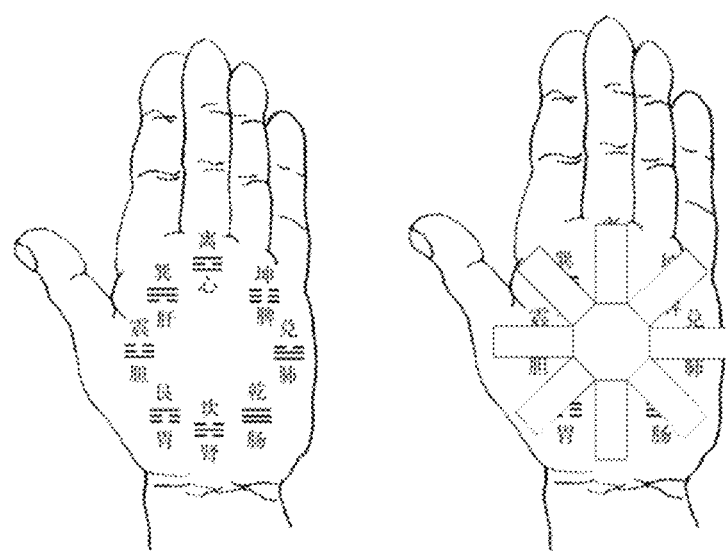

FIG. 8 is a sample view of the Eight-Trigrams with 5-Color Combination illustration on Palm.

Figure 9:
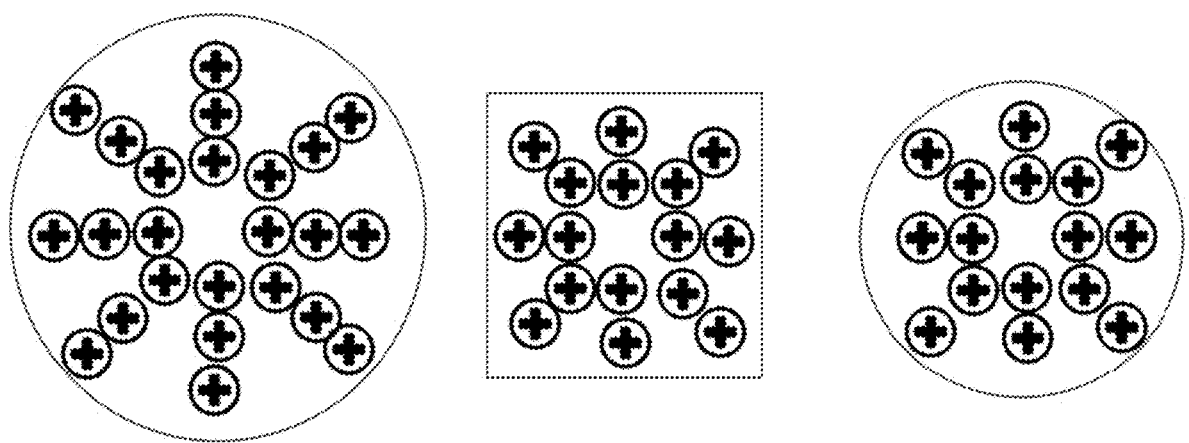

FIG. 9 is top perspective views of the Sample Design Diagrams for 5-Color Therapy Light-Emitting Component Positions.

✦: Single Emitting Component that can emit different color of lights.

Figure 10A:
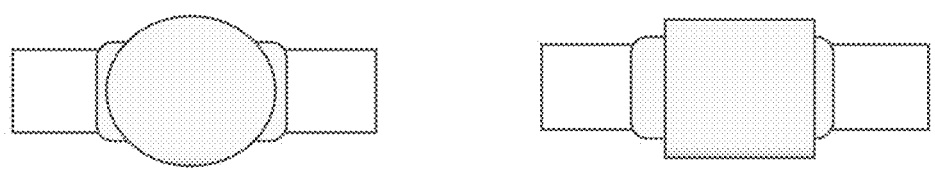
Figure 10B:

FIG. 10 is top views (FIG. 10A) and bottom views (FIG. 10B) of the designed Five-Color Photherapy Device.

DETAILED DESCRIPTION OF THE PREFERRED EMBODIMENTS

This invention creates a method and device that can provide steady energy source with five (5) different color schemes on Eight (8) Trigrams, easy and long duration of usage with related software that user can easily pick up the right color scheme for healing. This invention is to leverage the Photon which is the light energy source to implement the Five Element Color Therapy in active mode to heal the body and bring balance back to Human Body.

A photherapy device and related APP (the software) solution has been created as an Active Five Element Color Therapy method to balance and heal the Human Body.

With modern technology and concept, LED Lights have been applied to the photherapy device to provide the five (5) colors on Eight (8) Trigrams, a Bluetooth Module has been put into device so that related APP running on iOS or Android smartphones can communicate with the photherapy device, a wearable design and battery rechargeable module are also implemented into the device.

The photherapy device is designed based on Arduino ESP32 motherboard and tailored to incorporate LEDs on the back of the board, a Four-layered PCB (Printed Circuit Board) was created for it.

First-Layered Circuit is for ESP32 control modules with Battery management and rechargeable module. Second-Layered is mainly for power supplier. Third-Layered is for Ground®. Fourth-Layered is for LED control modules and LED Display Modules.

A firmware software was created running on ESP32 Module to control the LEDs, Communicate with APPs via Bluetooth Module and monitor the PCB functions in general.

3D Printing Case and Wearable Band Stripe are included in this photherapy device.

The light-emitting components on each Eight-Trigrams position can be either square, round or rectangle in continuous or non-continuous manner.

Based on the 5-Colors (plus empty color or no color) and Eight-Trigram positions, there will be totally 1,679,616 combinations as the Color Therapy Formula to treat the body and bring body back to balance. In order to implement the black light emitting source, a black color-like film has been equipped to the light-emitting components which emit white color light through the film to create the black light in need.

The invented photherapy device comprises: an enclosure or case and a wearable band stripe, wherein a circuit board secured within said enclosure; wherein said circuit board includes an arrangement of Eight-Trigram positions with multiple light-emitting components symmetric configured to provide photodynamic stimulation of a surface and underlying layers of cells of skin tissue, wherein the stimulation of light energy increasing the activity of cells and propagate the same effects to entire body for healing; wherein a battery-powered or USB (Universal Serial Bus) Connector receives DC Power and a power switch electrically connected to said multiple of light-emitting components though a single current limiting circuit; wherein operating current of each of said different wavelength light emitting components is from the single current limiting circuit; wherein a microprocessor powered by above power source on the circuit board will receive machine-instructions to control the light-emitting components should be lighted up with what wavelength for different light color to display; wherein the machine-instructions sent to Microprocessor can be either through USB (Universal Serial Bus), Microwave, Bluetooth, Infrared or WiFi (Wireless Fidelity for Internet networking) from either direct attached Screen Display or remote devices; wherein said photherapy device could be controlled or communicated by another remote device.

Such photherapy device has said circuit board which is configured to operate all of said light-emitting components with only a single positive, a single negative and a single signal connection from said power switch and from said printed circuit board; wherein all of the said light emitting components are contained on a printed circuit board; wherein said printed circuit board has electrical connections for as many as light-emitting components, wherein said light-emitting components are placed in a repeating and symmetric pattern, and close proximity in an eight-trigram positions; wherein said light-emitting components are connected in groups of at least one light-emitting component; wherein said light-emitting component could be LED (Light-Emitting Diodes) or any new materials that can emit various color of light in need; wherein said light-emitting component could be as small as a cell or to very large in combination with single or multiple light-emitting components to cover the entire body or area; wherein the light-emitting components on each Trigrams position can be either square, round, opal or rectangle in continuous or non-continuous and in symmetric formation.

The current invented phototherapy device could be used on Palm or Back of Hand, Forehead, Chest or on abdominal area along the center line of the body.

Such phototherapy device, wherein said light-emitting components transmit light in the wavelengths of 620-630 nm, 510-520 nm, and 570-580 nm, with Kelvin color temperature of 4000K-4500K, provides pain relief for a group of indications including arthritic pain, shoulder pain, lumber pain, menstruation pain, tooth pain, headache, stomach pain, sprain ankle pain, bruising pain, etc.

Such phototherapy device can be used to promote Qi and Blood Circulation, increase Immune system and to boost up Body Energy to prevent Etiology and against Pathogenesis causation. Such Etiology includes but not limited to Seven Emotional Factors (Anger, Joy, Melancholy, Worry, Grief, Fear and Fright), Six Exogenous Factors (Wind, Cold, Summer Heat, Damp, Dryness and Fire), Improper Diet, Overstrain, Stress and Lack of Physical Exercise, Traumatic Injury and Insect or Animal Bites, Phlegm Fluid and Stagnant Blood. Such Pathogenesis includes but not limited to Disharmony of Yin and Yang, Conflict between Antipathogenic Qi and Pathogenic Qi, Abnormal Ascending or Descending of Qi.

Such phototherapy device can also reduce post-op scarring, inflammation and redness; healing sores in the mouth; reduce and eliminate bruise; clear sinuses, constipation, Coughing, Dizziness, Diarrhea, Fever, Headache, Stye (Hordeolum), Gout, UTI (Urinary Tract Infection), Frequent Urination, Allergies, Prostate Enlargement (Swollen), Eczema, Flu, Dryness, Herpes Roster, Drunk, Itching, High Blood Pressure, Menopause Syndrome, Insomnia, Asthma, Stroke Sequelae, Impotence, etc.

In summary, the present invention provides a novel device for Five-Color Phototherapy based on Eight-Trigrams. It is wearable with band stripe and controllable with related software APP. Although this device and the method of using the same according to the present invention have been described in the foregoing specification with considerable details, it is to be understood that modifications may be made to the invention which do not exceed the scope of the claims and modified forms of the present invention done by others skilled in the art to which the invention pertains will be considered infringements of this invention when those modified forms fall within the claimed scope of this invention.

What is claimed is:

1. A five-color phototherapy device comprises an enclosure, a wearable band strap, and a circuit board secured within said enclosure, wherein said enclosure has a shape of square or round or oval or rectangle; wherein said wearable band strap is connected with two sides of said enclosure; wherein said circuit board is a four-layered printed circuit board which consists of a layer of control modules for battery management and rechargeable module, a layer for power supplier, a layer for ground, a layer of light control modules and light display modules; wherein said circuit board includes an arrangement of Eight-Trigram positions with multiple light-emitting components symmetric configured to provide photodynamic stimulation to a surface of a person's skin tissue; wherein said multiple light-emitting components are a number of light-emitting elements arranged on said circuit board symmetrically only in said Eight-Trigram positions; wherein said multiple light-emitting components only produce color of red or green or white or yellow or black or no color in each said Eight-Trigram position; wherein a plurality of different colors or no color can be applied to each Eight-Trigram position; wherein said plurality of colors comprise a red color or green color or white color or yellow color or black color or no color that is applied in each Eight-Trigram position; wherein said five-color phototherapy device is powered by a battery or by DC power through a USB connector; wherein each of said multiple light-emitting components on each Eight-Trigrams position is square or round or oval or rectangle in shape and is placed repeatedly in continuous or non-continuous symmetric formation; wherein a power switch is electrically connected to said multiple of light-emitting components through a single current limiting circuit which operates each of different wavelength light-emitting components; wherein a microprocessor on said circuit board receives machine-readable instructions to control the light-emitting components with related wavelengths for different colors to display; wherein a microprocessor on said circuit board is configured to receive machine-readable instructions configuring a red color or green color or white color or yellow color or black color or no color in each Eight-Trigram position to create the Five Elements relationships for therapeutic purpose; wherein said machine-readable instructions are sent to said microprocessor is through USB (Universal Serial Bus) or microwave or a short-range wireless interconnection or infrared or WiFi (Wireless Fidelity for Internet networking) from either a directly attached screen display or a remote device; wherein said five-color phototherapy device is controlled or in communication with a remote device; wherein said light-emitting component is a LED (Light-Emitting Diodes) or any equivalent materials that can emit the various colors of light required; wherein said five-color phototherapy device is used on a person's palm or back of hand or forehead or chest or abdominal area along the center line of a person's body; wherein said five-color phototherapy device is controlled by a software or an APP in a remote device or a smartphone.

* * * * *